(12) United States Patent  (10) Patent No.: US 8,351,571 B2
Brinks et al.  (45) Date of Patent: Jan. 8, 2013

(54) MOTION ESTIMATION IN TREATMENT PLANNING

(75) Inventors: Ralph Brinks, Hagen (DE); Carsten Meyer, Aachen (DE); Alexander Fischer, Aachen (DE); Daniel Gagnon, Twinsburg, OH (US); Marc Busch, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 696 days.

(21) Appl. No.: 12/525,825

(22) PCT Filed: Jan. 25, 2008

(86) PCT No.: PCT/IB2008/050279
§ 371 (c)(1),
(2), (4) Date: Aug. 5, 2009

(87) PCT Pub. No.: WO2008/096285
PCT Pub. Date: Aug. 14, 2008

(65) Prior Publication Data
US 2010/0054412 A1  Mar. 4, 2010

Related U.S. Application Data

(60) Provisional application No. 60/888,560, filed on Feb. 7, 2007.

(51) Int. Cl.
*A61N 5/10* (2006.01)
*G21K 5/10* (2006.01)
*H05G 1/08* (2006.01)

(52) U.S. Cl. ........................................................ 378/65

(58) Field of Classification Search ................. 378/65, 378/95, 69
See application file for complete search history.

(56) References Cited

U.S. PATENT DOCUMENTS

| | | | |
|---|---|---|---|
| 6,144,875 A * | 11/2000 | Schweikard et al. | 600/427 |
| 6,298,260 B1 | 10/2001 | Sontag et al. | |
| 6,385,286 B1 * | 5/2002 | Fitchard et al. | 378/65 |
| 6,473,636 B1 | 10/2002 | Wei et al. | |
| 6,961,405 B2 * | 11/2005 | Scherch | 378/65 |
| 2004/0254773 A1 | 12/2004 | Zhang et al. | |
| 2004/0267113 A1 | 12/2004 | Thomson | |
| 2005/0226485 A1 | 10/2005 | Boese | |
| 2006/0074292 A1 | 4/2006 | Thomson et al. | |

(Continued)

FOREIGN PATENT DOCUMENTS

EP  1520516 A1  4/2005

(Continued)

OTHER PUBLICATIONS

Kubo, et al., Respiration gated radiotherapy treatment: a technical study, Phys. Med. Biol., 1996, pp. 83-91, vol. 41.

(Continued)

*Primary Examiner* — Thomas R Artman

(57) ABSTRACT

An apparatus includes a scanner (102, 104) and a scanning motion monitor (100). A motion modeler (116) uses data from the scanning motion monitor (100) and the scanner (102, 104) to generate a motion model which describes motion of a region of interest of an object. A treatment planner (112) uses image data from the scanner (102, 104) to establish a treatment plan for the object. A treatment device 114, which operates in conjunction with a treatment motion monitor (108), uses the motion model to compensate for motion of the object during application of the treatment.

32 Claims, 4 Drawing Sheets

U.S. PATENT DOCUMENTS

| | | | |
|---|---|---|---|
| 2006/0074299 A1* | 4/2006 | Sayeh | 600/426 |
| 2006/0074304 A1 | 4/2006 | Sayeh | |
| 2006/0182326 A1 | 8/2006 | Schildkraut et al. | |
| 2006/0241379 A1 | 10/2006 | Greiser et al. | |
| 2010/0054412 A1* | 3/2010 | Brinks et al. | 378/65 |

FOREIGN PATENT DOCUMENTS

| | | |
|---|---|---|
| WO | WO 2005030330 A1 * | 4/2005 |
| WO | 200511554 A1 | 12/2005 |

OTHER PUBLICATIONS

Jacobs, et al., A fast algorithm to calculate the exact radiological path through a pixel or voxel space, Journal of computing and information technology, 1998, 12 pages, vol. 6, No. 1., University Computing Center, Zagreb, Croatie.

Minohara, et al., Respiratory gated irradiation system for heavy-ion radiotherapy, Int. J. Radiation Oncology Biol. Phys., 2000, pp. 1097-1103, vol. 47, No. 4, Elsevier Science, Inc.

Parodi, et al., Potential application of PET in quality assurance of proton therapy, Phys. Med. Biol., 2000, pp. N151-N156, vol. 45.

Langen et al., Organ motion and its management, Int. J. Radiation Oncology Biol. Phys., 2001, pp. 265-278, vol. 50, No. 1, Elsevier Science, Inc.

Grozinger, vol. conformal irradiation of moving target volumes with scanned ion beams, dissertation, Technischen Universitat Darmstade, 2004, 191 pages.

Lambert, et al., Intrafractional motion during proton beam scanning, Phys. Med. Biol. 2005, pp. 4853-4862, vol. 50, Institute of Physics Publishing.

Paganetti, et al., Proton beam radiotherapy—the state of the art, New Technologies in Radiation Oncology (Medical Radiology Series), Oct. 2005, 26 pages.

Grozinger, et al., Simulations to design an online motion compensation system for scanned particle beams, Phys. Med. Biol., 2006, pp. 3517-3531, vol. 51, Institute of Physics Publishing.

Jarritt, et al., The role of PET/CT scanning in radiotherapy planning, The British Journal of Radiology, Special Issue, 2006, pp. 527-535, vol. 79.

Varian Medical Systems, On-board imager kv imaging system, published on or before download date Jan. 25, 2007, 2 pages, http://www.varian.com/orad/prd172.html.

Calypso Medical, Calypso 4D localization system—GPS for the body, published on or before the download date Jan. 25, 2007, 2 pages, http://www.calypsomedical.com/products/default.asp.

Radiotherapy and Oncology; Elsevier; 2006; vol. 81; pp. S212-S213.

Seppenwoolde, Y., et al.; Precise and Real-Time Measurement of 3D Tumor Motion in Lung Due to Breathing and Heartbeat, Measured During Radiotherapy; 2002; Intl. J. of Radiation: Oncology Biology Physics; vol. 53:822-834.

Chen, C. W., et al.; Epicardial Motion and Deformation Estimation from Coronary Artery Bifurcation Points; 1990; Beckman Institute and Coordinated Science Laboratory; U. of Illinois; 456-459.

Puentes, J., et al.; Dynamic Feature Extraction of Coronary Artery Motion Using DSA Image Sequences; 1998; IEEE Trans. on Medical Imaging; 17(6)857-871.

* cited by examiner

MOTION ESTIMATION IN TREATMENT PLANNING

CROSS REFERENCE TO RELATED APPLICATIONS

This application claims the benefit of U.S. Provisional Application Serial No. 60/888,560 filed Feb. 7, 2007, which is incorporated herein by reference.

DESCRIPTION

The present application relates to motion estimation in treatment and treatment planning. While it finds particular application to the use of positron emission tomography (PET) data to estimate motion in connection with external radiotherapy in medicine, it also relates to other applications in which it is desirable to account for the effects of motion of an object.

In medical applications, structural medical imaging modalities such as computed tomography (CT) and magnetic resonance (MR) are widely used to generate image data indicative of the internal morphology of a patient. One application for this data is radiation therapy planning (RTP) in oncology, in which the image data has been used to calculate a spatially varying radiation dose to be applied to a tumor or other lesion. The calculated dose has been applied to the patient using therapy techniques such as intensity modulated radiotherapy (IMRT). These techniques have been used to more closely tailor the treatment to the requirements of a particular situation, for example, to apply a relatively higher dose to a desired portion of a tumor and reduce the effects of the treatment on surrounding healthy tissue.

A more recent trend has been the use of functional information in therapy planning. Information from a functional imaging modality such as positron emission tomography (PET) provides information indicative of the functional characteristics of a tumor, and more particularly the spatial variation of a functional characteristic. This information can in turn be used to better identify regions of the tumor where an increased dose should be applied, or stated conversely, may be treated with a relatively lower dose. As one example, current research indicates that hypoxic tissues within a tumor may be relatively resistant to treatment. It is thus desirable to apply a relatively higher dose to regions of the tumor that contain such tissues.

However, the target volume can be affected by patient motion, as for example periodic respiratory motion. To compensate for the effects of such motion, and to ensure that the desired clinical target volume receives the desired dose, a planning margin has been established, with the dose applied to the relatively larger volume. Unfortunately, however, such an approach can be injurious to otherwise healthy tissue. Moreover, such motion also tends to reduce the accuracy with which a spatially varying dose can be applied to the desired regions of the tumor.

Aspects of the present application address these matters and others.

In accordance with one aspect, a method includes correlating projection data acquired during an examination of an object with a measured motion of the object and using the correlated projection data to model a motion of a first region of interest of the object.

According to another aspect, an apparatus includes a grouper, a filter, a characteristic processor, and a position determiner. The grouper groups projection data indicative of an interior of an object according to a motion of the object measured during the acquisition of the projection data. The filter selects projection data that is indicative of a first region of interest of the object. The characteristic processor uses the selected projection data to identify a characteristic feature of the first region of interest. The position determiner determines a position of the identified feature as a function of the measured motion.

According to another aspect, a computer readable storage medium contains instructions which, when executed by a computer, cause the computer to carry out a method. The method includes grouping projection data indicative of radionuclide decays in an object according to a motion of the object, selecting projection data that is indicative of radionuclide decays occurring in a first region of interest of the object, using the selected projection data to identify a characteristic feature of the first region of interest, and using the grouped projection data to determine a position of the identified feature as a function of the motion.

According to another aspect, a method for correcting for motion in an image reconstructed from raw data includes identifying a first region of an object, identifying a second region of the object, using the raw data to estimate a characteristic feature of the first region, using the estimated characteristic feature to correct raw data indicative of the second region to compensate for a motion of the second region, and using the corrected raw data to reconstruct a motion-corrected image of the second region.

According to another aspect, a computer readable storage medium contains instructions which, when executed by a computer, cause the computer to carry out a method. The method includes using first projection data representative of the decay of a first radioactive tracer in an object to model a motion of the object and using the modeled motion to correct second projection data representative of the decay of a second radionuclide in the object.

According to another aspect, a method includes using projection data acquired during an imaging examination of an object to estimate a characteristic feature of a region of interest of the object, determining a trajectory of the characteristic feature, and presenting the determined trajectory in a human readable form.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIGS. 5A-D depict motion trajectories.

Figure 6:
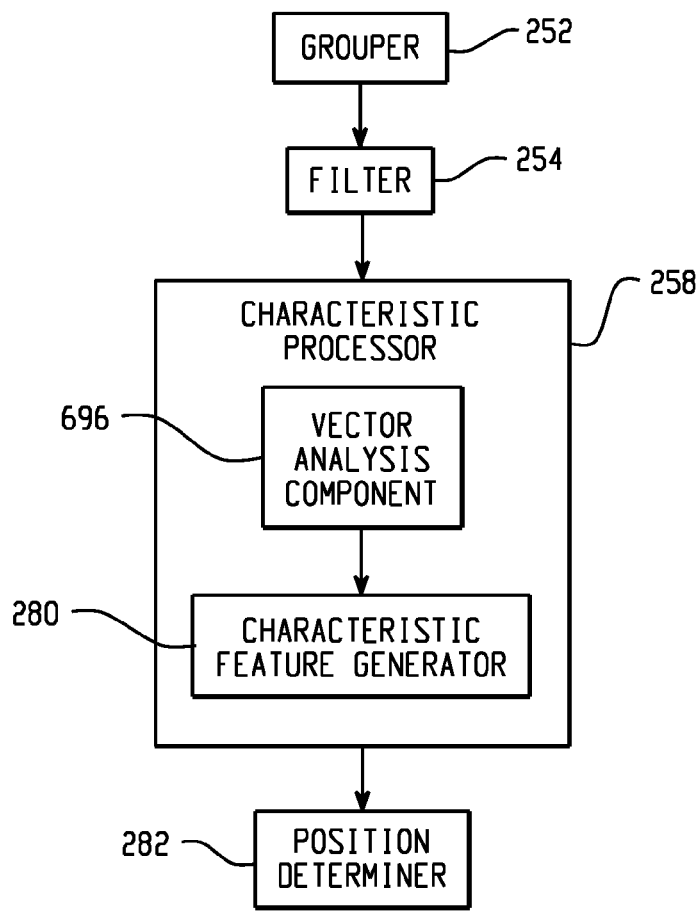

FIG. 6 is a block diagram of a motion modeler.

Figure 7:
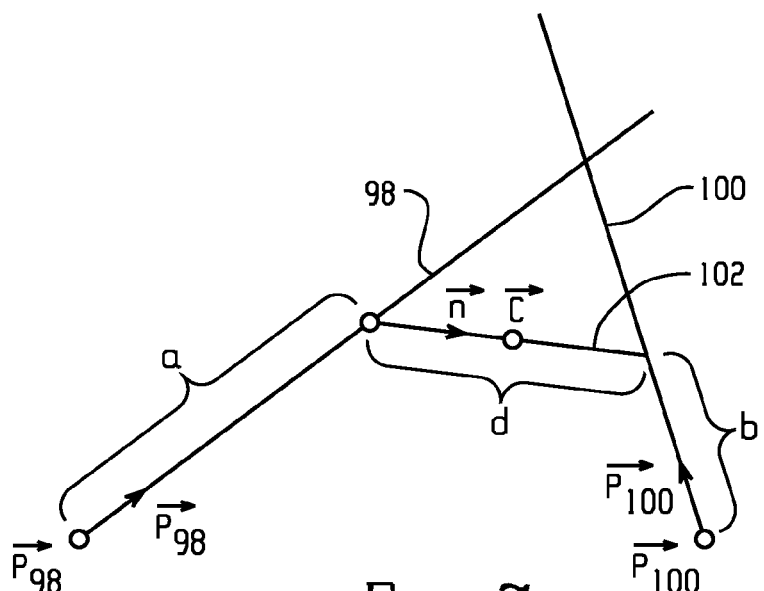

FIG. 7 depicts vectors.

Figure 1:
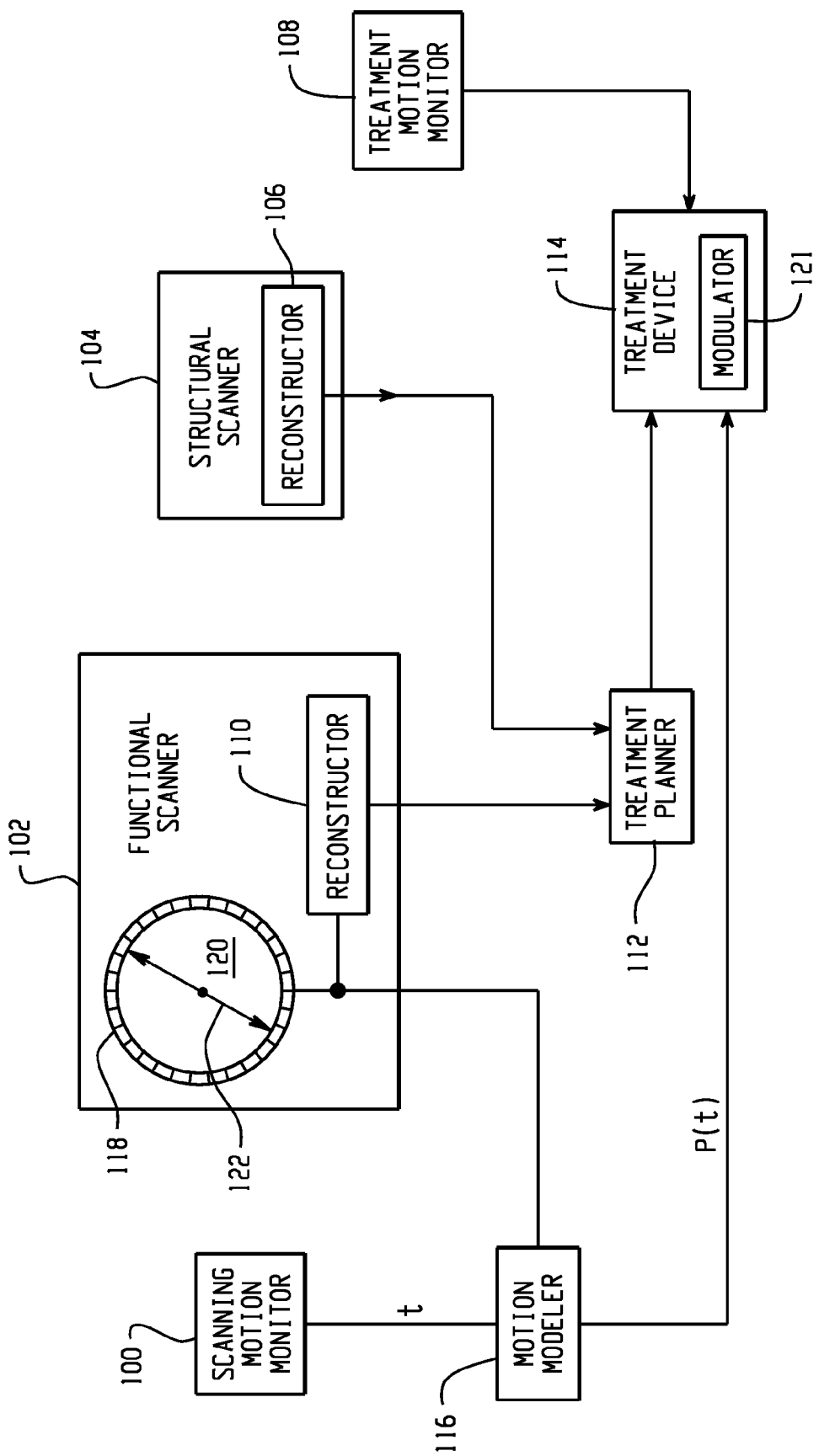
FIG. 1 is a block diagram of a diagnosis and treatment system.

With reference to FIG. 1, a system 100 includes a functional imaging modality scanner 102, a structural imaging modality scanner 104, a motion monitor 100, a scanning motion modeler 116, and a treatment planner 112.

As illustrated in FIG. 1, the functional imaging modality scanner 102 is a PET scanner. PET scanners conventionally include a plurality of radiation sensitive detectors 118 disposed about an examination region 120 in a generally ring or cylindrically shaped arrangement. In connection with a PET examination, a tracer which includes a positron emitting radionuclide is introduced into the object under examination. As the radionuclide decays, the emitted positrons interact with electrons in what are known as positron annihilations, with the annihilations generating pairs of temporally coincident 511 kiloelectron volt (keV) gamma rays which travel in substantially opposite directions along a line of response (LOR) 122. Where the imager 102 is a time of flight (TOF) PET scanner, a time of flight detector measures the arrival times of the coincident photons, with the resultant information being used to estimate the position of the annihilation along the LOR 122.

The functional imaging scanner 102 generates raw or projection data indicative of the detected annihilations. In the case of a list mode acquisition, the raw data includes a list of the many annihilations detected in the course of a given scan, with the entries in the list typically contain information indicative of the location and orientation of the LOR 122, the location of the event along the LOR 122 (particularly in the case of a TOF system), the time at which the annihilation was detected, and other relevant information.

A reconstructor 110 reconstructs the raw data using a suitable iterative, analytical, or other reconstruction technique to generate volumetric image data indicative of the object.

The structural imaging modality scanner 104 includes a CT, MR, or other scanner which generates projection data indicative of the structure of the object. A reconstructor 106 reconstructs the raw data to produce volumetric image data indicative of the object using reconstruction techniques which are appropriate for the scanner 104 modality.

Note that the functional 102 and structural 104 imaging modality scanners may be combined in a single scanner, for example in the case of a PET/CT, PET/MR or other hybrid modality scanner.

The scanning motion monitor 100, which measures a motion of the object in connection with a scan, operates in conjunction with the functional 102 and/or structural 104 scanners so that projection data acquired during the course of a given scan can be correlated with the motion state of the object. It will be appreciated that the form and function of the scanning motion monitor 100 depends on the object being monitored and the nature of the monitored motion. The monitor 100 may measure the motion indirectly, for example by way of one or more mechanical, electrical, or other sensors that sense dynamic or time varying features indicative of the motion of interest. In the case of a human patient, for example, the motion monitor 100 may include a physiological monitor which measures physiological signal(s) indicative of a physiological motion of interest. A respiratory monitor, for example, may include a chest belt or other device which senses the periodic mechanical motion associated with breathing, a temperature sensor which measures the temperature of the patient's respiratory air, or the like. In the case of cardiac motion, the motion monitor 100 may measure an electrocardiogram (ECG) signal.

As will be described further below, the motion modeler 116 uses projection data from the functional scanner 102 and the information from the motion monitor 100 to generate a local motion model representative of a region of interest of the object. Where the motion is modeled in three spatial dimensions, the motion model can be expressed according to the relation:

$$P(t) = (x(t), y(t), z(t)) \quad \text{Equation 1}$$

where P(t) is position of the region of interest as a function of time, and x(t), y(t), and z(t) represent the position of the region of interest along respective x, y, and z axes. In the case of periodic motion, the temporal component may be expressed in relation to the motion phase. It will also be appreciated that the motion model may be expressed other than in terms of absolute position (e.g., in terms of positional differences, velocities, accelerations or the like) and in relation to other desired coordinate systems.

The treatment planner 112 uses the image data from the functional 102 and/or structural scanners 104 to plan a treatment to be applied to the object. In the case of an RTP system used in radiation oncology, the treatment plan typically includes a spatially varying radiation dose which is to be applied to a tumor or other lesion.

With continuing reference to FIG. 1, the system 100 also includes a treatment device 114 and a treatment motion monitor 108.

The treatment motion monitor 108 is analogous to the scanning motion monitor 100, with its nature and configuration again depending on the nature of the object and the motion being monitored. Note that the scanning 100 and treatment 108 motion monitors may be implemented as a single device, for example where a single motion monitor is transported from location to location or where one or more of the scanners 102, 104 and the treatment device 114 are located in physical proximity.

The treatment device 114 applies the desired treatment to the object. More specifically, the object is typically positioned in a known position and orientation with respect to the treatment device 114. Depending again on the object to be treated and the nature of the treatment, such positioning may be facilitated, by way of fiducial markers, positioning devices which conform to a portion of the object (e.g., a conformal face mask in the case of a therapy to be applied to the head of a human patient), other restraints, auxiliary imaging devices which provide structural or other image data, or other suitable techniques. The treatment device 114 uses motion information from the motion model P(t) and the treatment motion monitor 108 to compensate for object motion during the course of the applied treatment. In the case of respiratory motion of a human patient, for example, the treatment device 114 would ordinarily compensate for the patient's respiratory phase.

As illustrated in FIG. 1, the treatment device 114 includes a modulator 121 which modulates an intensity or other characteristic of the treatment applied to the object, for example by modulating a spatial, temporal, and/or other characteristic of the applied dose so that the applied treatment approximates that calculated by treatment planner 112. Again in relation to the example of external radiation therapy in oncology, the treatment device 114 may include an intensity modulated radiation therapy device. Such devices typically include a multi-leaf collimator which is used to modulate the applied radiation so as to apply the desired radiation dose to the tumor. Other treatment devices, including but not limited to linear accelerators, particle therapy devices, radio frequency ablation or other devices, and high field ultrasound treatment devices are also contemplated.

Figure 2:
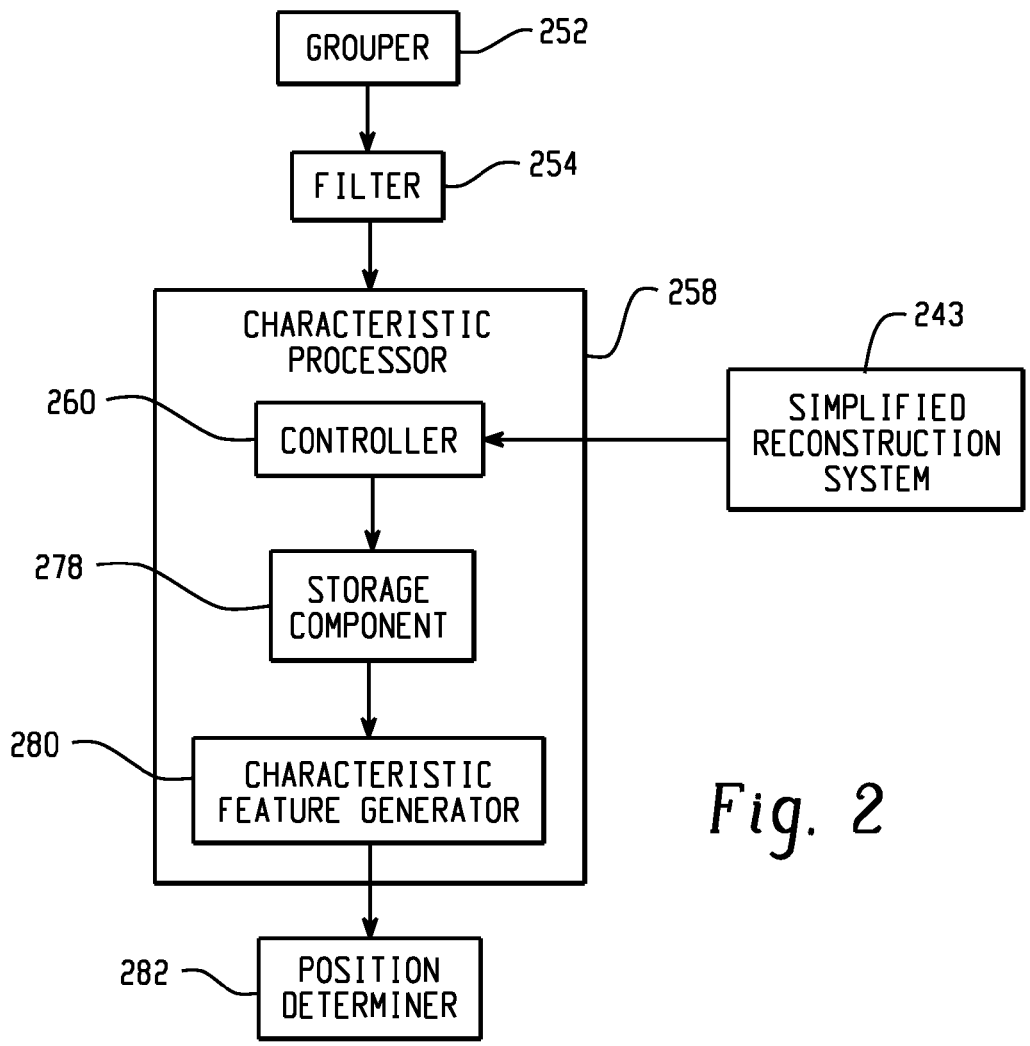
FIG. 2 is a block diagram of a motion modeler.

Turning now to FIG. 2, the motion modeler 116 includes a grouper 252, a filter 254, a characteristic processor 258, and a position determiner 282. The grouper 252 groups the projection data from the functional scanner 102 into temporally corresponding groups. Where the data includes list mode PET data, for example, the grouper 252 groups the various LORs into the appropriate temporal groups.

Note that, in the case of periodic motion, the motion period may be divided into a plurality of motion phases, with the projection data grouped according to the motion phase in which it was acquired. The temporal extent of the various groups may be, but is not necessarily, constant. Thus, groups which correspond to motion phases which are expected to exhibit relatively faster motion have a relatively shorter temporal duration. As another example, the motion phases may be grouped so that the number or amount or LORs or other projection data in each group is substantially constant. It will be appreciated, however, that other grouping schemes may also be implemented.

The filter 254 filters or disregards projection data that does not intersect (or stated conversely, selects projection data which does intersect) a user or automatically defined region of interest (ROI). Again in example of PET data in an oncology application, for example, the filter 254 selects those LORs which intersect an ROI which includes a tumor of interest. Where TOF data is available, those LORs for which the annihilation likely falls outside the ROI may be discarded.

A characteristic processor 258 determines a characteristic feature such as a center of mass or other center function of the projection data of each filtered group. As shown in the example of FIG. 2, a controller 260 of the characteristic processor 258 accesses a simplified reconstruction system 243. The simplified reconstructor 243 performs a locally constrained backprojection of the various groups of filtered projection data to generate partial images corresponding to the temporal groups. The partial images are stored in a storage component 278 such as a memory.

Figure 3:
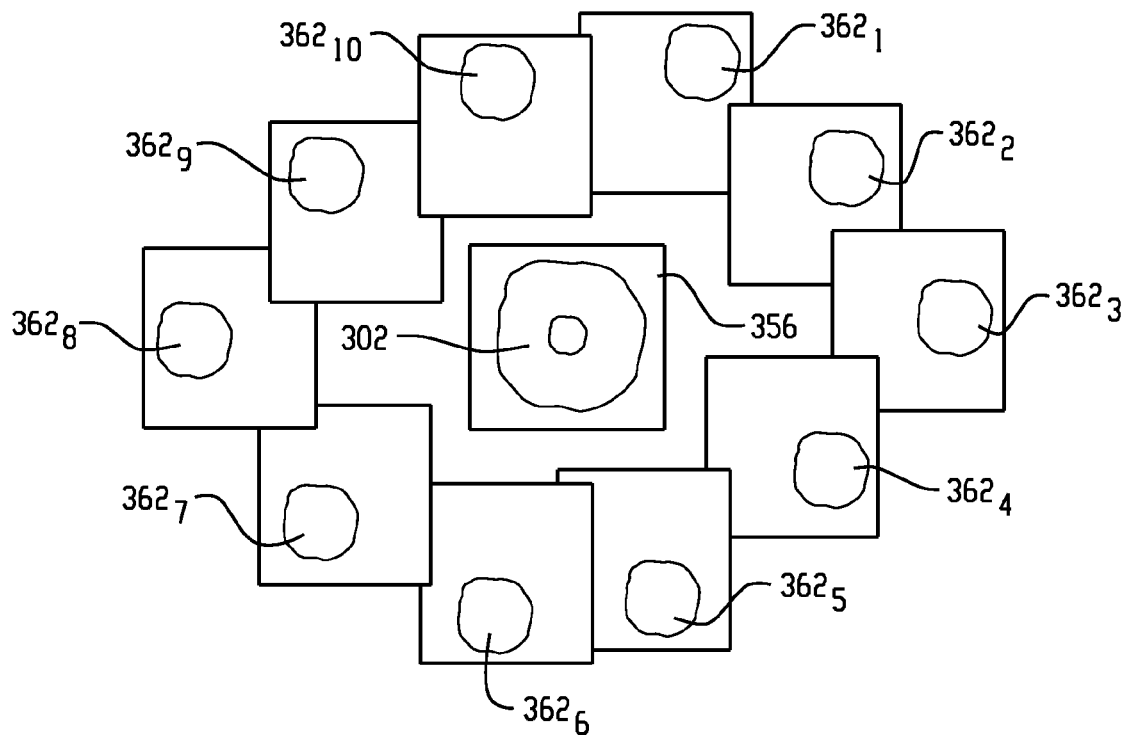
FIG. 3 depicts intermediate images.

FIG. 3 depicts one example of an ROI 356 and a plurality of intermediate images $362_{1-10}$ generated by the simplified reconstructor 243. In the example of FIG. 3, a tumor 320 undergoes a generally circular, clockwise motion in the ROI 356. While ten (10) intermediate images 362 are shown in FIG. 3 for the purposes of illustration, other numbers of temporal groups and/or intermediate images may also be generated. It will also be appreciated that FIG. 3 depicts an image slice of the ROI 356. Where the ROI 356 includes a volume, the reconstructed intermediate image data covering the volume would be reconstructed.

Figure 4:
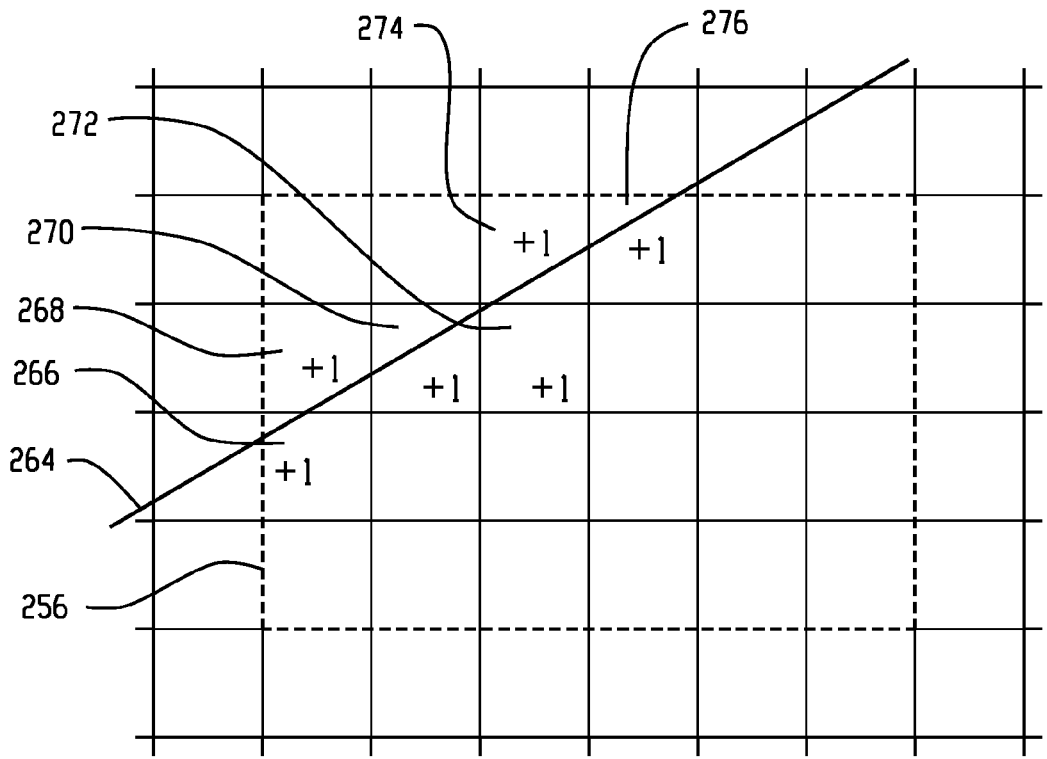
FIG. 4 depicts aspects of a technique for generating intermediate images.

In one implementation, the distance over which the various projections intersect the voxels of the ROI 256 is calculated, with the simplified reconstructor 243 updating the voxel values as a function of the calculated distance. In a simplified implementation, the value of a given voxel is incremented or otherwise increased uniformly each time a projection intersects the voxel. This is illustrated in FIG. 4 again in the example case of a PET system where an LOR 264 intersects voxels 266, 268, 270, 272, 274, and 276 of the ROI 256. Note that the voxel weighting produced by the simplified reconstructor 243 may also take into account TOF data, if available.

Returning to FIG. 2, a characteristic feature generator 280 computes a center of mass, center of activity, or other characteristic feature of the various partial images. Depending on the selected simplified reconstruction technique, and to reduce the effects of projection data indicative of regions outside the ROI 256, it may be desirable to consider only a subset of the voxels in the ROI when calculating the characteristic feature. This may be accomplished, for example, by way of a thresholding technique in which those voxels having a value less than a user selected or other desired percentage of the maximum voxel value of the ROI are not considered.

The motion determiner 282 uses the characteristic feature data to generate the motion model P(t), with the motion model being stored in a computer readable memory accessible to or otherwise provided to the treatment device 114.

FIG. 6 depicts an alternative embodiment of the motion modeler 116, with like reference numerals describing items analogous to those described above in relation to FIG. 2.

As illustrated, the characteristic processor 258 includes a vector analysis component 696 which receives the filtered projection data generated by the filter 254. Again in the context of LORs generated in PET imaging, it will be assumed that each LOR can be described by a point $\vec{P}_x$ on the LOR and a unit vector $\vec{p}_x$ which describes its direction. FIG. 7 illustrates two such LORs, with a first LOR 98 described by point $\vec{P}_{98}$ and unit vector $\vec{p}_{98}$ and a second LOR 100 described by point $\vec{P}_{100}$ and unit vector $\vec{p}_{100}$.

Point $\vec{C}$ represents the center of the shortest line segment 102 connecting the first 98 and second 100 LORs:

$$\vec{C} = \vec{P}_{98} + b \cdot \vec{p}_{98} - \frac{d}{2}\vec{n}, \qquad \text{Equation 2}$$

where d is the length of the line segment connecting the LORs 98 and 100:

$$d = |(\vec{P}_{98} - \vec{P}_{100}) \cdot \vec{n}|, \qquad \text{Equation 3}$$

n is a unit vector pointing in the direction of the line segment connecting the LORs 98 and 100:

$$\vec{n} := \vec{P}_{98} \times \vec{P}_{100} / |\vec{P}_{98} \times \vec{P}_{100}|, \qquad \text{Equation 4}$$

and b is defined by:

$$b = \frac{\left[ P_{98}^y - P_{100}^y + dn^y + (P_{100}^x - P_{98}^x - dn^x)\frac{p_{98}^y}{p_{98}^x} \right]}{\left( p_{100}^y - \frac{p_{100}^x p_{98}^y}{p_{98}^x} \right)}, \qquad \text{Equation 5}$$

Returning to FIG. 6, the vector analysis component 696 generates a collection of points {C1, C2, . . . Cn} for n successive pairs of LORs, thereby generating a point cloud.

Note that parallel LORs or LORs perpendicular to the x-axis are treated separately.

The characteristic feature generator 280 determines the center or mass or other desired characteristic feature of the point cloud. If desired, outlying points may be disregarded when determining the center of mass. The motion determiner 282 again uses the characteristic feature data to generate the motion model P(t).

Suitable techniques for determining a motion of a region of interest are also disclosed in commonly owned U.S. Provisional Patent Application Ser. No. 60/777,469 filed on Feb. 28, 2006 and entitled Local Motion Compensation Based on List Mode Data, which application is expressly incorporated by reference in its entirety herein. The motion model P(t) may also be used by the reconstructors 110, 106 to compensate for motion in the reconstructed images. In the case of data from a PET scanner, for example, the motion model P(t) can be used to shift the positions of LORs indicative of events occurring in the ROI so as to compensate for the detected motion. All or a desired portion of the acquired data set is then reconstructed.

The techniques described above may also be applied to acquisitions in which the projection data is sorted or binned into a plurality of bins. In such an implementation, a plurality of sets of bins would be established, with each set corresponding to a desired time period or motion phase. The grouper 252 would then operate at the time of or in connection with the data acquisition to sort or bin the projection data into the appropriate bin as a function of its location or other characteristic(s) and a time at which a particular projection data was received.

The techniques are also applicable to single photon emission tomography (SPECT) and other functional and structural modalities. They are also applicable to other treatment modalities.

There may be situations in which it is relatively difficult to effectively identify a specific lesion or other feature of the object in order to establish the motion model. Such a situation may arise, for example, in relatively specific, low intensity PET studies involving the use of labeled monoclonal antibodies, stem cell monitoring, or other molecular imaging techniques which produce relatively few low intensity hot spots and limited, if any, anatomical references.

Lesions or other hot spots may also be blurred by motion of the object, with such blurring tending to reduce the average intensity of the hot spot. The reduction in intensity may in many cases lead to the non-identification of the hot spot or otherwise complicate its detection. Consequently, a motion correction may be applied to regions known to have or suspected of having one or more relatively weaker or unidentified hot spots. As the motion correction tends to intensify the relative weaker areas and thus aid in the identification of suspect regions, the motion corrected data may be analyzed to identify lesions or other features of interest.

Multiple agents may also be used. For example, first and second agents and/or isotopes may be introduced in the object in connection with a given scan. The first agent is used to produce the desired study data, while the second is used to identify the desired motion. More particularly, the second agent is selected for its affinity to a portion of the object in the vicinity of and which serves as a proxy for the motion of the ROI. In one such example, 18-F can be used to identify a structure such as a rib or other bone which can serve as a proxy for respiratory motion. In another, NH3 can be used to identify the myocardium in connection with cardiac motion.

In such an implementation, a first or motion ROI is established at the proxy region, with the motion corrector 116 operating on data from the motion ROI to generate the motion model P(t) as described above. Where the motion model P(t) is used in connection with the motion compensation of image data, a second or imaging ROI is established at the region being studied. The motion model P(t) is then used to shift or otherwise correct the projection data to compensate for motion in the imaging ROI. Suitable techniques for such compensation are also described in the patent application incorporated by reference above.

Figure 5A:
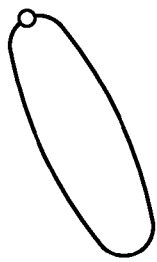
Figure 5B:
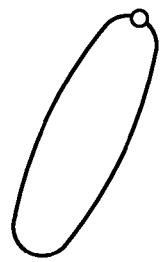
Figure 5C:

It may also be desirable to provide a clinician or other user with a graphical representation of the motion of a lesion or other feature of interest. Accordingly, the motion model P(t) may be plotted and displayed on a display, printout, film or other suitable human readable output device. One example of such a plot or motion track of a feature or interest in connection with a given scan is shown in FIGS. 5A, 5B, 5C where an arbitrary motion of a feature of interest is shown projected into three planes such as planes parallel to the x, y, and z planes of the motion model P(t). The plot may also be presented in relation to a single arbitrarily selected plane or surface, with movement in other directions presented by changing a color, thickness, or other characteristic of the motion plot.

Figure 5D:
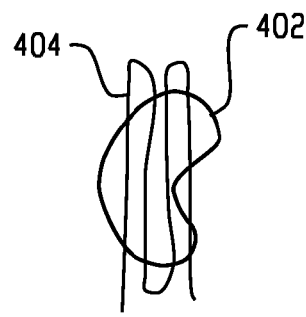

The desired plot(s) may also be superimposed on corresponding image(s) of the object. Doing so may be particularly useful in situations where the motion of a feature of interest may not be readily apparent from the image itself, as may occur in the case of a motion compensated image or in the case of a non-motion compensated image which exhibits significant blurring. Such a superimposed image is illustrated in FIG. 5D, where an arbitrary motion trajectory 404 is shown superimposed on motion compensated image of a feature of interest 402. While illustrated as being superimposed or overlayed on a relevant image, the motion may also be displayed in a separate window or in a distinct region of the display, adjacent the feature of interest, or the like. By way of one example, the feature of interest may include a lung tumor, while the motion trajectory depicts movement of the tumor due to respiratory motion.

Note that the various techniques described above may be implemented by way of computer readable instructions stored on suitable computer readable media. When executed by a computer processor, the instructions cause the computer processor to carry out the described techniques.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method comprising:
    correlating functional imaging projection data acquired during an examination of an object with a measured motion of the object to generate correlated functional imaging projection data;
    filtering the correlated functional imaging projection data to select data which intersects a first region of interest of the object;
    using the correlated selected functional imaging projection data to generate a model of a time varying feature of the first region of interest, including a vector analysis of the correlated selected functional imaging projection data to generate a collection of points comprising a point cloud, and further including determining a characteristic feature of the point cloud and using the determined characteristic point cloud feature to generate the model; and
    supplying the model to a treatment apparatus that applies a treatment to the object.

2. The method of claim 1 including
    measuring a motion of the object during the applied treatment; and
    using the measured motion and the motion model to adjust an operation of the treatment apparatus during the applied treatment.

3. The method of claim 1 wherein the measured motion is periodic and the method includes grouping the correlated selected functional imaging projection data according to a phase of the motion during which the correlated selected functional imaging projection data was acquired.

4. The method of claim 1 including displaying a trajectory of the time varying feature in a human readable form.

5. The method of claim 1 wherein the model of the time varying feature of the first region of interest serves as a proxy for a time varying feature of a second region of interest.

6. The method of claim 1 wherein the projection data includes list mode data indicative of radionuclide decays in the object.

7. The method of claim 1 including grouping the functional imaging projection data into temporal groups according to a motion of the object, and performing a locally constrained reconstruction of each temporal group to generate a partial image corresponding to the temporal group.

8. The method of claim 1 wherein the functional imaging projection data is comprised of voxels, the method further including applying a threshold which discards voxels having a value which is less than a minimum value before application of the using step.

9. The method of claim 1 wherein the functional imaging projection data includes lines of response, and the vector analysis includes determining spatial relationships between the lines of response and using the determined spatial relationships to generate the point cloud.

10. An apparatus comprising:
a grouper that groups functional imaging projection data indicative of an interior of an object according to a motion of the object measured during an acquisition of the projection data;
a filter that selects functional imaging projection data that is indicative of a first region of interest of the object;
a characteristic processor that uses the selected functional imaging projection data to identify a characteristic feature of the first region of interest, wherein the characteristic processor includes:
a vector analysis component adapted to receive the selected functional imaging projection data and to perform a vector analysis on the selected functional imaging projection data to generate a collection of points comprising a point cloud; and
a characteristic feature generator adapted to identify the characteristic feature of the first region of interest by determining a characteristic feature of the point cloud; and
a position determiner that determines a position of the identified feature as a function of the measured motion.

11. The apparatus of claim 10 including a hybrid modality scanner that generates the functional imaging projection data.

12. The apparatus of claim 10 including an external radiotherapy apparatus that modulates a therapy applied to the object as a function of the determined position and a motion of the object measured during the applied therapy.

13. The apparatus of claim 10 wherein the measured motion is a physiological motion and the functional imaging projection data includes time of flight positron emission tomography data.

14. The apparatus of claim 10 including means for displaying a motion of the identified feature.

15. The apparatus of claim 10 including a simplified reconstruction system that performs a locally constrained reconstruction of each group of data generated by the grouper.

16. The apparatus of claim 15 wherein the functional imaging projection data is comprised of voxels, and the simplified reconstruction system assigns a weight value to each voxel corresponding to a number of image projections which intersect the voxel, and applies a threshold which discards voxels having a weight value which is less than a minimum value before the reconstruction.

17. The apparatus of claim 10 wherein the functional imaging projection data includes lines of response, and the vector analysis includes determining spatial relationships between the lines of response and using the determined spatial relationships to generate the point cloud.

18. A non-transitory computer readable storage medium containing instructions which when executed by a computer cause the computer to carry out a method that includes:
grouping functional imaging projection data indicative of radionuclide decays in an object according to a motion the object;
selecting the functional imaging projection data that is indicative of radionuclide decays occurring in a first region of interest of the object;
using the selected functional imaging projection data to identify a characteristic feature of the first region of interest, including a vector analysis of the selected functional imaging projection data to generate a collection of points comprising a point cloud, and including determining a characteristic feature of the point cloud and using the determined characteristic point cloud feature to identify the characteristic feature of the first region of interest; and
using the grouped functional imaging projection data to determine a position of the identified feature of the first region of interest as a function of the motion.

19. The non-transitory computer readable storage medium of claim 18 wherein the determined position of the first region of interest serves as a proxy for a position of a second region of interest.

20. The non-transitory computer readable storage medium of claim 18 wherein the method includes plotting a trajectory of the determined position on an image which includes the first region of interest.

21. The non-transitory computer readable storage medium of claim 18 wherein the method includes storing the determined position in a non-transitory computer readable memory accessible to a treatment apparatus.

22. The non-transitory computer readable storage medium of claim 18 wherein the method includes performing a locally constrained reconstruction of each group of data.

23. The non-transitory computer readable storage medium of claim 18 wherein the functional imaging projection data is comprised of voxels, the method further including applying a threshold which discards voxels having a value which is less than a minimum value before identifying a characteristic feature of the first region of interest.

24. The non-transitory computer readable storage medium of claim 18 wherein the functional imaging projection data includes lines of response, and the vector analysis includes determining spatial relationships between the lines of response and using the determined spatial relationships to generate the point cloud.

25. A method for correcting for motion in an image reconstructed from functional imaging raw data, the method comprising:
identifying a first region of an object in the functional imaging raw data;
identifying a second region of the object in the functional imaging raw data;
using the functional imaging raw data to estimate a characteristic feature of the first region, including a vector analysis of the first region functional imaging raw data to generate a collection of points comprising a point cloud, and including determining a characteristic feature of the point cloud and using the determined characteristic point cloud feature to estimate the characteristic feature of the first region;
using the estimated characteristic feature of the first region to correct functional imaging raw data indicative of the second region to compensate for a motion of the second region; and
using the corrected raw data to reconstruct a motion-corrected image of the second region.

26. The method of claim 25 wherein using the functional imaging raw data includes
grouping the functional imaging raw data into a plurality of temporal groups; and using the grouped functional imaging raw data to perform locally constrained reconstructions of the first region.

27. The method of claim 25 wherein the functional imaging raw data includes lines of response and the vector analysis includes determining spatial relationships between the lines of response; and using the determined spatial relationships to generate the point cloud.

28. The method of claim 25 wherein the method includes concurrently presenting an image of the second region and a motion of the estimated characteristic feature in human readable form.

29. The method of claim 25 wherein the functional imaging raw data includes raw data representative of decays of a first radioactive tracer having an affinity for the first region and decays of a second, different tracer having an affinity for the second region.

30. The method of claim 25 including correlating the functional imaging raw data with a measured motion of the object;

using the correlated functional imaging raw data to generate a motion model; and supplying the motion model to a treatment apparatus.

31. The method of claim 25 wherein the functional imaging raw data includes lines of response representative of radionuclide decays and using the estimated characteristic feature includes generating a motion model that models a motion of the characteristic point cloud feature;

identifying lines of response that intersect the second region; and using the motion model to vary a position of the identified lines of response.

32. The method of claim 25 wherein the functional imaging raw data is list mode projection data.

\* \* \* \* \*